United States Patent
Zhang et al.

(10) Patent No.: US 10,508,112 B2
(45) Date of Patent: *Dec. 17, 2019

(54) INTERMEDIATE COMPOUNDS FOR PREPARATION OF PRAZIQUANTEL AND PROCESSES FOR PREPARING THE INTERMEDIATE COMPOUNDS

(71) Applicants: Zhejiang Hisun Pharmaceutical Co., Ltd., Taizhou, Zhejiang (CN); Shanghai Institute of Pharmaceutical Industry, Shanghai (CN)

(72) Inventors: Fuli Zhang, Shanghai (CN); Zhezhou Yang, Shanghai (CN); Rusheng Bao, Taizhou (CN); Weiwei Xu, Taizhou (CN); Hua Bai, Taizhou (CN)

(73) Assignees: Zhejiang Hisun Pharmaceutical Co., Ltd., Taizhou, Zhejiang (CN); Shanghai Institute of Pharmaceutical Industry, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/014,678

(22) Filed: Jun. 21, 2018

(65) Prior Publication Data

US 2018/0297998 A1 Oct. 18, 2018

Related U.S. Application Data

(62) Division of application No. 15/550,190, filed as application No. PCT/CN2015/072830 on Feb. 12, 2015, now Pat. No. 10,035,798.

(51) Int. Cl.
| | |
|---|---|
| *C07C 237/22* | (2006.01) |
| *C07D 471/04* | (2006.01) |
| *A61K 31/4985* | (2006.01) |
| *C07C 231/02* | (2006.01) |
| *C07C 231/14* | (2006.01) |

(52) U.S. Cl.
CPC ........ *C07D 471/04* (2013.01); *A61K 31/4985* (2013.01); *C07C 231/02* (2013.01); *C07C 231/14* (2013.01); *C07C 237/22* (2013.01)

(58) Field of Classification Search
CPC .................................................. C07C 237/22
USPC ....................................................... 562/450
See application file for complete search history.

(56) References Cited

U.S. PATENT DOCUMENTS

| 4,049,659 A | 9/1977 | Pohlke |
| 4,362,875 A | 12/1982 | Seubert |
| 10,035,798 B2 * | 7/2018 | Zhang ................ A61K 31/4985 |

FOREIGN PATENT DOCUMENTS

| CN | 1683346 A | 10/2005 |
| CN | 103044422 A | 4/2013 |
| CN | 103739601 A | 4/2014 |
| DE | 2504250 A1 | 8/1976 |
| DE | 2508947 A1 | 9/1976 |
| KR | 20020076486 A | 10/2002 |
| RU | 2425825 C2 | 8/2011 |
| WO | 2008096231 A1 | 8/2008 |
| WO | 2012081035 A2 | 6/2012 |

OTHER PUBLICATIONS

Extended European Search Report dated Jul. 17, 2018 in EP Application No. 15881512.6.
Kim et al., "Formation of Pyrazinoisoquinoline Ring System by the Tandem Amidoalkylation and N-Acyliminium Ion Cyclization: An Efficient Synthesis of Praziquantel," Tetrahedron, vol. 54, pp. 7395-7400 (1998).
Written Opinion dated Nov. 17, 2015 in Int'l Application No. PCT/CN2015/072830.
Int'l Search Report dated Nov. 17, 2015 in Int'l Application No. PCT/CN2015/072830.
Wang, Dong-sheng, "Progress of Research on Synthesis of Praziquantel," Chemical World, vol. 4, pp. 249-251 (2008) (English Abstract).
Wang, et al., "Synthesis of Antischistosomal Praziquantel," Journal of Shanghai Institute of Technology (Natural Science), vol. 13, No. 2, pp. 113-117 (2013) (English Abstract).
Office Action dated Jan. 14, 2019 in CN Application No. 201580075573.3.
Office Action dated Nov. 1, 2018 in KR Application No. 10-2017-7025578.
Office Action and Search Report dated Jun. 26, 2018 in RU Application No. 2017131412.
Office Action dated Apr. 22, 2019 in IN Application No. 201717029344.
Office Action dated May 9, 2019 in EP Application No. 15881512.6.

* cited by examiner

*Primary Examiner* — Jeffrey H Murray
(74) *Attorney, Agent, or Firm* — Panitch Schwarze Belisario & Nadel LLP

(57) ABSTRACT

Intermediate compounds for the preparation of Praziquantel are provided. In particular, the intermediate compounds provided include a compound of formula (IV) and a compound of formula (V). Also provided are processes for preparing the intermediate compounds. Additionally, the raw materials are inexpensive and easy to obtain, the key intermediates are easy to prepare, and the total reaction yield and purity of the obtained target compound Praziquantel is high, so that industrialized mass production of Praziquantel using the intermediate compounds is easy to achieve.

14 Claims, No Drawings

INTERMEDIATE COMPOUNDS FOR PREPARATION OF PRAZIQUANTEL AND PROCESSES FOR PREPARING THE INTERMEDIATE COMPOUNDS

CROSS-REFERENCE TO RELATED APPLICATION

This application is a Divisional of co-pending U.S. patent application Ser. No. 15/550,190, filed Aug. 10, 2017, which was a Section 371 of International Application No. PCT/CN2015/072830, filed Feb. 12, 2015, which was published in the Chinese language on Aug. 18, 2016, under International Publication No. WO 2016/127350 A1, the disclosure of which is incorporated herein by reference in its entirety.

TECHNICAL FIELD

The present invention belongs to the field of medicinal synthesis and relates to a process for preparing the antiparasitic agent Praziquantel and the intermediate thereof. Particularly, the invention relates to an improved process for preparing Praziquantel and the intermediate compounds such as those of formula IV, formula V as well as a process for preparing the intermediate compounds and the use thereof.

BACKGROUND

Praziquantel is a broad spectrum antiparasitic agent useful for treating schistosomiasis japonica, schistosomiasis haematobia, schistosomiasis mansoni, paragonimiasis, clonorchiasis sinensis, hydatidosis, cysticercosis, sparganosis mansoni, fasciolopsiasis, trichomoniasis or the like, particularly schistosomiasis japanica and clonorchiasis *sinensis*. Praziquantel was firstly commercially available as "Cesol" in Germany in 1980 and became the first option for treating helminthiasis, which has the chemical structure of formula I:

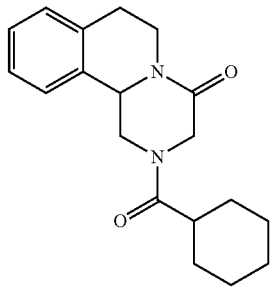

DE 2504250 and DE 2508947 disclose a process for synthesizing Praziquantel using isoquinoline as starting material, which was widely used in the world. Nevertheless, the process has long processing with up to 8 steps and thus a yield as low as about 15%. During the processing, hypertoxic chemicals like cyanide is used and operation is performed under high pressure and thus this process is dangerous and prone to accident. Additionally, the process has the disadvantages like pollutants emissions and high cost for environment protection and thus is greatly limited in its industrial scaling up.

KR 2002076486 discloses a process for synthesizing Praziquantel using β-phenethylamine, chloroacetyl chloride, aminoacetaldehyde dimethyl acetal and the like as starting materials, which has relatively less reaction steps without using cyanide. However, the aminoacetaldehyde dimethyl acetal used in this process is expensive with low reactivity and selectivity and requires high reactive temperature causing side reaction and thus is not suitable for industrial production.

CN 1683346A discloses a process for synthesizing Praziquantel using β-phenethylamine, aminoacetyl halide hydrochloride, halogenated acetaldehyde acetal and cyclohexanecarbonyl chloride as starting materials with the steps of condensation, cyclization, acylation. The process is simple, environment-friendly and has less steps with total yield over 50%. However, the starting material halogenated acetaldehyde acetal is expensive with low reactivity and selectivity and the starting material aminoacetyl halide hydrochloride is not stable and prone to deterioration. Therefore, the process is not suitable for industrial production.

SUMMARY

In view of the disadvantages in the prior art, in an aspect, provided is an improved process for preparing Praziquantel. The process is advantageous, for example it is reasonably designed, simple, cost-effective, environment-friendly and requires moderate reaction conditions as well as cheap and easily obtainable starting materials. Moreover, the intermediates are easy to be prepared, the total yield is high (≥60%), the target product compound of formula I Praziquantel has a high purity (HPLC purity ≥99.8%). Therefore, the process is suitable for industrial production at large scale.

Particularly, provided is a process for preparing Praziquantel, comprising the steps of:

1) subjecting β-phenethylamine and chloroacetyl chloride to condensation reaction in the presence of alkaline substance to give the compound of formula II;

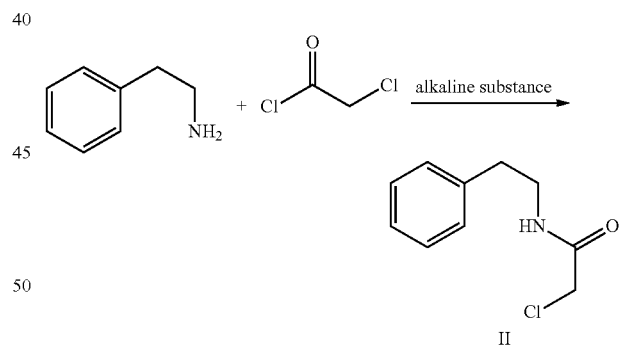

2) subjecting the compound of formula II and ethanolamine to substitution reaction to give the compound of formula III;

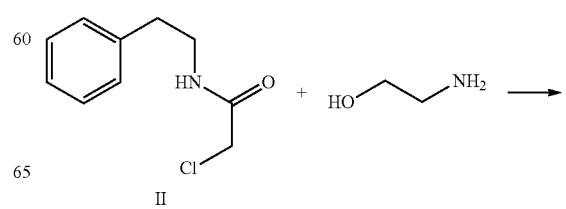

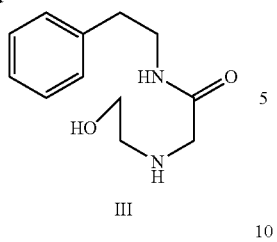

III 3) subjecting the compound of formula III and cyclohexanecarbonyl chloride to acylation reaction in the presence of alkaline substance to give the compound of formula IV;

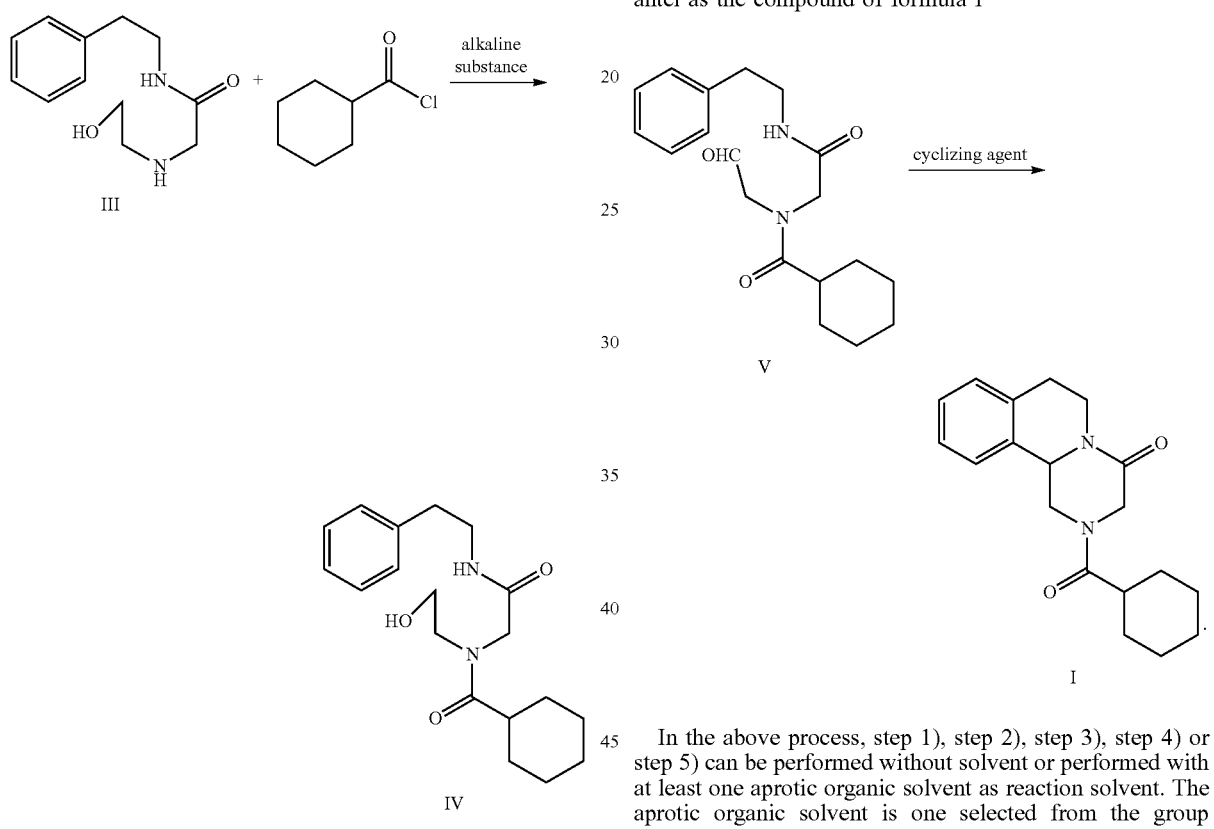

4) subjecting the compound of formula IV to oxidation reaction in the presence of oxidizing agent to give the compound of formula V; and

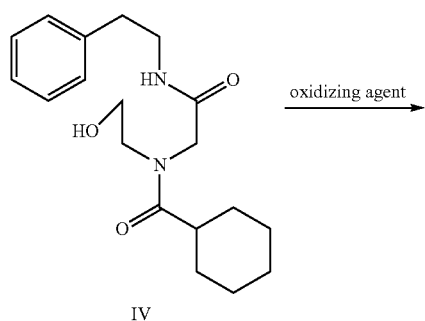

IV

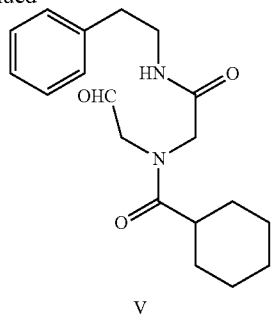

V 5) subjecting the compound of formula V to cyclization reaction in the presence of cyclizing agent to give Praziquantel as the compound of formula I In the above process, step 1), step 2), step 3), step 4) or step 5) can be performed without solvent or performed with at least one aprotic organic solvent as reaction solvent. The aprotic organic solvent is one selected from the group consisting of ethers solvent, aromatic hydrocarbons solvent, hydrocarbons or halogenated hydrocarbons solvent or esters solvent; wherein the ethers solvent is selected from the group consisting of tetrahydrofuran, diethyl ether, 1,2-dimethoxyethane, methyl tert-butyl ether or 2-methyltetrahydrofuran, preferably methyl tert-butyl ether; the aromatic hydrocarbons solvent is selected from the group consisting of benzene, toluene, ethylbenzene or xylene, preferably toluene; the hydrocarbons or halogenated hydrocarbons solvent is selected from the group consisting of n-hexane, cyclohexane, n-heptane, dichloromethane, trichloromethane or dichloroethane, preferably dichloromethane; the esters solvent is selected from the group consisting of methyl formate, ethyl formate, methyl acetate, ethyl acetate or isopropyl acetate, preferably ethyl acetate or isopropyl acetate.

Preferably, in the above process, step 2) is performed without solvent. Preferably, step 1), step 3), step 4) or step 5) is performed using at least one aprotic organic solvent as reaction solvent.

In the above process, the reaction temperature of step 1), step 2), step 3), step 4) or step 5) is −10° C. to 100° C., preferably 0° C. to 40° C., more preferably 5° C. to 15° C., most preferably 10° C. to 15° C.

Preferably, in the above process, step 1), step 2), step 3), step 4) or step 5) is performed under ice water bath, room temperature or 0° C. to 40° C.

In the above process, step 1), step 3) or step 5) is preferably performed under ice water bath, step 2) is preferably performed at room temperature, step 4) is preferably performed at 0° C. to 40° C., more preferably 5° C. to 15° C., most preferably 10° C. to 15° C.

In the above process, the alkaline substance in step 1), step 3) is one or more selected from the group consisting of: triethylamine, imidazole, pyridine, 2-methylpyridine, 2,6-dimethylpyridine, 4-dimethylaminopyridine, diisopropylamine, dimethylisopropylamine, diisopropylethylamine, NaOH, Na$_2$CO$_3$, NaHCO$_3$, KOH or K$_2$CO$_3$, preferably one selected from the group consisting of triethylamine, NaOH, Na$_2$CO$_3$, NaHCO$_3$, KOH or K$_2$CO$_3$.

In the above process, the molar ratio of the compound of formula II in step 2) to ethanolamine is 1:2-1:15, preferably 1:3-1:8.

In the above process, the oxidizing agent in step 4) is at least one group selected from the group consisting of: NaClO/TEMPO/NaBr, Ca(ClO)$_2$/TEMPO/NaBr, TCCA/TEMPO, NaNO$_2$/FeCl$_3$/TEMPO/air, NaNO$_2$/FeCl$_3$/TEMPO/O$_2$ or DMSO/SO$_3$-Py/Et$_3$N. The "NaClO/TEMPO/NaBr" refers to the combination of NaClO, TEMPO and NaBr, and other expressions should be explained in a similar way. The component TEMPO in the oxidizing agent used in oxidation reaction refers to TEMPO and derivative thereof, for example one or more selected from the group consisting of TEMPO, 4-OH-TEMPO, 4-(4-methylbenzenesulfonyloxy)-TEMPO, 4-acetylamino-TEMPO, 4-benzoyloxy-TEMPO, 4-NH$_2$-TEMPO, 4-oxy-TEMPO or 4-methanesulfonyloxy-TEMPO.

In the above process, the cyclizing agent in step 5) is one or more selected from the group consisting of: formic acid, acetic acid, trifluoroacetic acid, methanesulfonic acid, trifluoromethanesulfonic acid, p-toluenesulfonic acid, benzenesulfonic acid, perchloric acid or concentrated sulfuric acid, preferably concentrated sulfuric acid or methanesulfonic acid.

In another aspect, provided is key intermediate compound of formula IV for preparing Praziquantel.

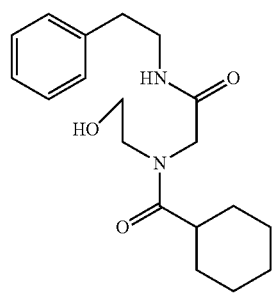

IV

The compound of formula IV can be prepared by the following process: using β-phenethylamine as starting material, the compound of formula IV is obtained through condensation, substitution and acylation reactions. In the process, the alkaline substance, reaction temperature, reaction solvent, molar ratios of the reactants can be used according to the process for preparing Praziquantel as mentioned above and will not be repeated. A person skilled in the art will make modification or improvement to the preparing process according to the prior art or to prepare the key intermediate i.e. the compound of formula IV by other synthesis process.

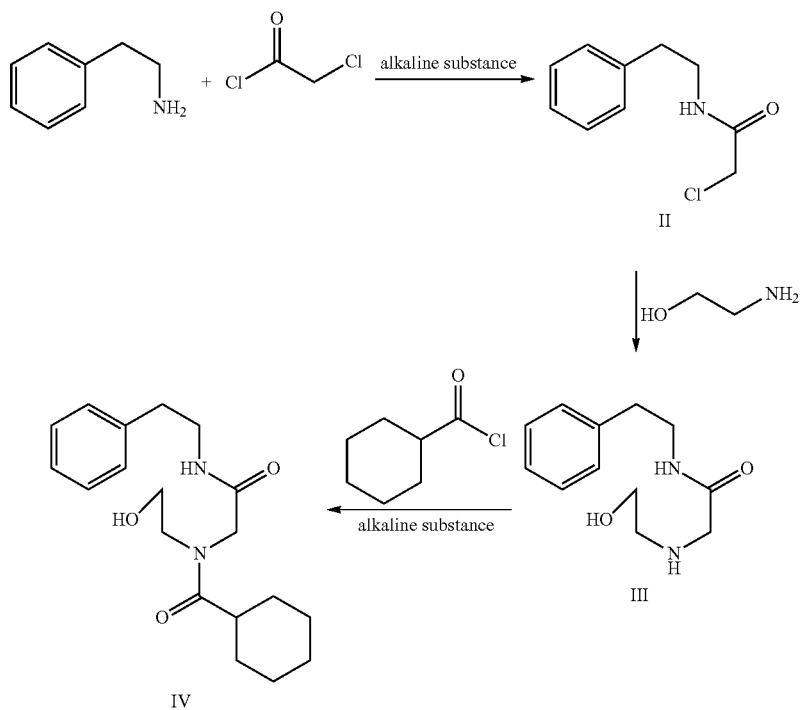

In another aspect, provided is the key intermediate compound of the formula V for preparing Praziquantel:

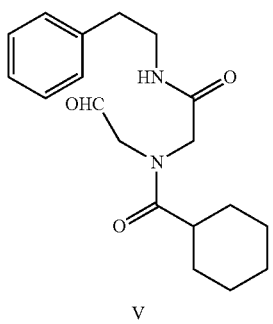

V

The compound of formula V can be prepared by the following process: the compound of formula V is obtained through oxidation reaction of the above compound of formula IV in the presence of oxidizing agent. In the process, the oxidizing agent, reaction temperature, reaction solvent or the like can be used according to the process for preparing Praziquantel as mentioned above. The preparation of the compound of formula IV can be referred to the above contents and will not be repeated.

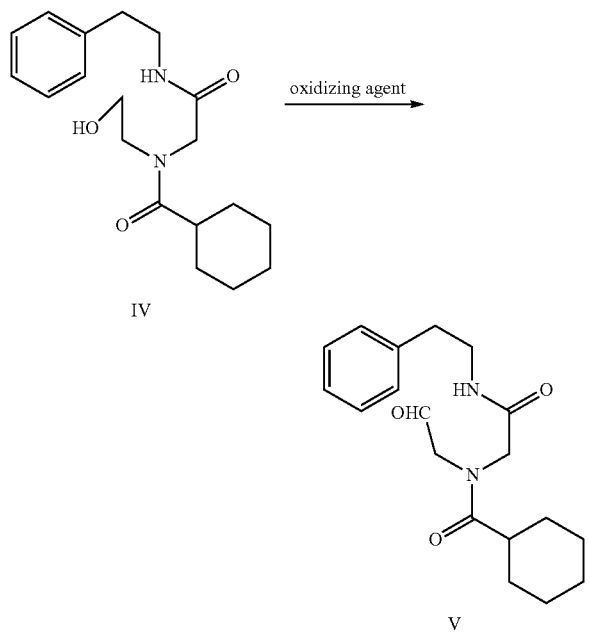

In a further aspect, provided is use of the compound of formula IV in the preparation of antiparasitic agent Praziquantel.

In yet a further aspect, provided is use of the compound of formula V in the preparation of antiparasitic agent Praziquantel.

The process for preparing Praziquantel according to the invention is reasonably designed, cost-effective, environment-friend, and requires cheap and easily obtainable starting materials. Particularly, the intermediates compounds of formula IV and formula V can be easily prepared, with high total yield (≥60%), the target product of Praziquantel has a high purity (HPLC purity ≥99.8%). Therefore, the process is suitable for industrial production at large scale.

DETAILED DESCRIPTION

The invention will be further illustrated by the following Examples, which however should not be understood as any limitation thereto. A person skilled in the art can make modification or improvement according to the prior art, which are within the scope of the invention. The protection scope and spirit are defined by the claims and the technical solutions equivalent thereto.

$^1$HNMR is recorded with AM 400 Nuclear Magnetic Resonance Spectrometer with the chemical shift shown as δ (ppm).

Mass spectrum is determined through Shimadzu LCMS-2010 HPLC-MS.

The terms used in the description and claims are provided as follows. Unless stated otherwise, other undefined terms have the general meaning in the art.

TEMPO: 2,2,6,6-tetramethylpiperidine-1-oxyl free radical

TCCA: trichloroisocyanuric acid $SO_3$-Py: sulfur trioxide pyridine

The above reagents are purchased from Sinopharm Chemical Reagent Co., Ltd.

Example 1

Step 1): to a 500 ml reaction bottle were successively added β-phenethylamine (15.36 g, 126.75 mmol), $CH_2Cl_2$ (150 ml) and NaOH (7.30 g, 182.50 mmol), to which was added dropwise chloroacetyl chloride (15.0 g, 132.80 mmol) under ice water bath. After addition, the reaction was performed for 1 h. Then to the reaction liquid was added 150 ml water and the mixture was stirred and allowed to stand and the organic layer was separated. The organic layer was washed with diluted hydrochloric acid aqueous solution (50 ml) and then with water (100 ml×2), dried with anhydrous magnesium sulfate, filtered and concentrated to give 24.73 g of the compound of formula II as white solid (yield: 98.7%).

$^1$HNMR (CDCl$_3$) δ: 2.86(t, 2H), 3.57(q, 2H), 4.02(s, 2H), 6.59(s, 1H), 7.20-7.35(m, 5H). MS (ESI) m/z: 198.07([M+1]$^+$), 220.05([M+Na]$^+$)

Step 2): To a 250 ml reaction bottle were successively added the compound of formula II prepared above (22.90 g, 115.85 mmol) and ethanolamine (42.60 g, 697.45 mmol) and the mixture was stirred at room temperature for 12 h. The ethanolamine was distilled off under reduced pressure to give 23.67 g of the compound of formula III as yellow oil (yield 91.9%).

$^1$HNMR(CDCl$_3$) δ: 2.37(s, 2H), 2.64(t, 2H), 2.83(t, 2H), 3.23(s, 2H), 3.44(s, 1H), 3.51-3.58(m, 4H), 7.20-7.32(m, 5H).

MS (ESI) 223.15([M+1]$^+$), 245.13([M+Na]$^+$)

Step 3): To a 500 ml reaction bottle were successively added the compound of formula III prepared above (18.50 g, 83.23 mmol), $CH_2Cl_2$ (150 ml) and triethylamine (12.64 g, 124.91 mmol), to which was added dropwise cyclohexanecarbonyl chloride (12.77 g, 87.10 mmol) under ice water bath. After addition, the reaction was performed for 2 h. To the reaction liquid was added diluted hydrochloric acid aqueous solution (150 ml), which was then stirred and allowed to stand. The organic layer was separated, washed with water (100 ml×2), dried with anhydrous magnesium sulfate, filtered and concentrated. The resulting solid was slurried with methyl tert-butyl ether to give 25.62 g of the compound of formula IV as white solid (yield 92.6%).

$^1$HNMR(CDCl$_3$) δ: 1.20-1.79(m, 10H), 2.58(m, 1H), 2.81 (t, 2H), 3.49-3.58(m, 4H), 3.70(t, 2H), 3.83(s, 2H), 3.98(s, 1H), 6.48(s, 1H), 7.18-7.31(m, 5H).

MS (ESI) m/z: 333.23([M+1]$^+$), 355.21([M+Na]$^+$)

Step 4): To a 500 ml reaction bottle were successively added the compound of formula IV prepared above (10.20 g, 30.68 mmol), CH$_2$Cl$_2$ (150 ml), 15 wt % NaBr aqueous solution (10.53 g, 15.35 mmol) and TEMPO (0.05 g, 0.32 mmol) and the temperature in the bottle was controlled at 5-10° C. and then NaClO aqueous solution (180 g, 32.24 mmol) of which the pH had been adjusted to 8-9 with saturated NaHCO$_3$ aqueous solution was added dropwise. The reaction was performed for 20 h. The aqueous layer was separated and extracted with 30 ml CH$_2$Cl$_2$, The organic layer was combined, washed with sodium thiosulfate aqueous solution (100 ml×2), washed with water (100 ml×2), dried with anhydrous magnesium sulfate, filtered and concentrated to give 8.92 g of the compound of formula V as light yellow solid (yield 88.0%).

$^1$HNMR(CDCl$_3$) δ: 1.21-1.76(m, 10H), 2.43(m, 1H), 2.88-2.99(m, 2H), 3.21-3.65(m, 2H), 3.88-3.99(m, 2H), 4.32-4.80(m, 3H), 7.19-7.31(m, 5H)

MS (ESI) m/z: 331.21([M+1]$^+$), 353.19([M+Na]$^+$)

Step 5); To a 100 ml reaction bottle was added concentrated sulfuric acid (15 ml), to which was added dropwise the solution of the compound of formula V prepared above (5.60 g, 16.95 mmol) in CH$_2$Cl$_2$ (1.5 ml) under ice water bath. The reaction was performed for 8 h. The reaction liquid was poured into 150 ml of ice water and extracted with CH$_2$Cl$_2$ (50 ml×2). The organic layer was combined, washed with saturated Na$_2$CO$_3$ aqueous solution (50 ml), washed with water (50 ml×2), dried with anhydrous magnesium sulfate, filtered and concentrated to give light yellow solid, which was recrystallized with ethanol to give 4.45 g of the compound of formula I Praziquantel as white solid (HPLC purity 99.92%, yield 84.0%)

$^1$HNMR(CDCl$_3$) δ: 1.46-1.79 (m, 10H), 2.45(m, 1H), 2.75-3.01(m, 4H), 4.06(d, 1H), 4.45(d, 1H), 4.78-4.80(m, 2H), 5.15(dd, 1H), 7.16-7.26(m, 4H)

MS (ESI) m/z: 313.21([M+1]$^+$), 335.1.9([M+Na]$^+$)

Example 2

Except that the compound of formula II in step 1) was prepared according to the following procedures, other steps were the same as those of Example 1.

To a 500 ml reaction bottle were successively added β-phenethylamine (15.36 g, 126.75 mmol), CH$_2$Cl$_2$ (150 ml) and NaHCO$_3$ (21.30 g, 253.54 mmol), to which was added dropwise chloroacetyl chloride (15.0 g, 132.80 mmol) under ice water bath. After addition, the reaction was performed for 1 h. To the reaction liquid was added 150 ml of water, which was stirred and allowed to stand. The organic layer was separated and the organic phase was washed with diluted hydrochloric acid aqueous solution (50 ml), washed with water (100 ml×2), dried with anhydrous magnesium sulfate, filtered and concentrated to give 24.85 g of the compound of formula II as white solid (yield 99.2%).

Example 3

Except that the compound of formula II in step 1) was prepared according to the following procedures, other steps were the same as those of Example 1.

To a 500 ml reaction bottle were successively added β-phenethylamine (15.36 g, 126.75 mmol), CH$_2$Cl$_2$ (150 ml) and Na$_2$CO$_3$ (20.15 g, 190.11 mmol), to which was added dropwise chloroacetyl chloride (15.0 g, 132.80 mmol) under ice water bath. After addition, the reaction was performed for 1 h. Then to the reaction liquid was added 150 ml of water, which was stirred and allowed to stand. The organic layer was separated and the organic phase was washed with diluted hydrochloric acid aqueous solution (50 ml), washed with water (100 ml×2), dried with anhydrous magnesium sulfate, filtered and concentrated to give 24.38 g of the compound of formula II as white solid (yield 97.3%).

Example 4

Except that the compound of formula II in step 1) was prepared according to the following procedures, other steps were the same as those of Example 1.

To a 500 ml reaction bottle were successively added β-phenethylamine (15.36 g, 126.75 mmol), CH$_2$Cl$_2$ (150 ml) and K$_2$CO$_3$ (26.27 g, 190.07 mmol), to which was added dropwise chloroacetyl chloride (15.0 g, 132.80 mmol) under ice water bath. After addition, the reaction was performed for 1 h. Then to the reaction liquid was added 150 ml of water, which was stirred and allowed to stand. The organic layer was separated and the organic phase was washed with diluted hydrochloric acid aqueous solution (50 ml), washed with water (100 ml×2), dried with anhydrous magnesium sulfate, filtered and concentrated to give 24.45 g of the compound of formula II as white solid (yield 97.6%).

Example 5

Except that the compound of formula II in step 1) was prepared according to the following procedures, other steps were the same as those of Example 1.

To a 500 ml reaction bottle were successively added β-phenethylamine (15.36 g, 126.75 mmol), toluene (150 ml) and NaOH (7.30 g, 182.50 mmol), to which was added dropwise chloroacetyl chloride (15.0 g, 132.80 mmol) under ice water bath. After addition, the reaction was performed for 1 h. Then to the reaction liquid was added 150 ml of water, which was stirred and allowed to stand. The organic layer was separated and the organic phase was washed with diluted hydrochloric acid aqueous solution (50 ml), washed with water (100 ml×2), dried with anhydrous magnesium sulfate, filtered and concentrated to give 24.43 g of the compound of formula II as white solid (yield 97.5%).

Example 6

Except that the compound of formula II in step 1) was prepared according to the following procedures, other steps were the same as those of Example 1.

To a 500 ml reaction bottle were successively added β-phenethylamine (15.36 g, 126.75 mmol), methyl tert-butyl ether (150 ml) and NaOH (7.30 g, 182.50 mmol), to which was added dropwise chloroacetyl chloride (15.0 g, 132.80 mmol) under ice water bath. After addition, the reaction was performed for 1 h. Then to the reaction liquid was added 150 ml of water, which was stirred and allowed to stand. The organic layer was separated and the organic phase was washed with diluted hydrochloric acid aqueous solution (50 ml), washed with water (1.00 ml×2), dried with anhydrous magnesium sulfate, filtered and concentrated to give 24.25 g of the compound of formula II as white solid (yield 96.8%).

Example 7

Except that the compound of formula III in step 2) was prepared according to the following procedures, other steps were the same as those of Example 1.

To a 250 ml reaction bottle were successively added the compound of formula II prepared above (24.50 g, 123.95 mmol) and ethanolamine (30.28 g, 495.74 mmol), which was stirred at room temperature for 12 h. Ethanolamine was distilled off under reduced pressure to give 24.66 g of the compound of formula III as yellow oil (yield 89.5%).

Example 8

Except that the compound of formula III in step 2) was prepared according to the following procedures, other steps were the same as those of Example 1.

To a 250 ml reaction bottle were successively added the compound of formula II prepared above (12.70 g, 64.25 mmol) and ethanolamine (31.40 g, 514.08 mmol), which was stirred at room temperature for 12 h. Ethanolamine was distilled off under reduced pressure to give 13.25 g of the compound of formula III as yellow oil (yield 92.8%).

Example 9

Except that the compound of formula IV in step 3) was prepared according to the following procedures, other steps were the same as those of Example 1.

To a 500 ml reaction bottle were successively added the compound of formula III prepared above (28.60 g, 128.67 mmol), $CH_2Cl_2$ (300 ml) and NaOH (7.72 g, 193.0 mmol), to which was added dropwise cyclohexanecarbonyl chloride (19.81 g, 135.12 mmol) under ice water bath. After addition, the reaction was performed for 2 h. To the reaction liquid was added 150 ml of diluted hydrochloric acid aqueous solution, which was stirred and allowed to stand. The organic layer was separated, washed with water (100 ml×2), dried with anhydrous magnesium sulfate, filtered and concentrated. The resulting solid was slurried with methyl tert-butyl ether to give 40.42 g of the compound of formula IV as white solid (yield 94.5%).

Example 10

Except that the compound of formula IV in step 3) was prepared according to the following procedures, other steps were the same as those of Example 1.

To a 250 ml reaction bottle were successively added the compound of formula III prepared above (7.50 g, 33.74 mmol), $CH_2Cl_2$ (100 ml) and $NaHCO_3$ (5.67 g, 67.49 mmol), to which was added dropwise cyclohexanecarbonyl chloride (5.20 g, 35.47 mmol) under ice water bath. After addition, the reaction was performed for 2 h. To the reaction liquid was added 50 ml of diluted hydrochloric acid aqueous solution, which was stirred and allowed to stand. The organic layer was separated, washed with water (50 ml×2), dried with anhydrous magnesium sulfate, filtered and concentrated. The resulting solid was slurried with methyl tort-butyl ether to give 10.04 g of the compound of formula IV as white solid (yield 89.5%).

Example 11

Except that the compound of formula IV in step 3) was prepared according to the following procedures, other steps were the same as those of Example 1.

To a 250 ml reaction bottle were successively added the compound of formula III prepared above. (7.50 g, 33.74 mmol), toluene (250 ml) and NaOH (2.70 g, 67.49 mmol), to which was added dropwise cyclohexanecarbonyl chloride (5.20 g, 35.47 mmol) under ice water bath. After addition, the reaction was performed for 2 h. To the reaction liquid was added 50 ml of diluted hydrochloric acid aqueous solution, which was stirred and allowed to stand. The organic layer was separated, washed with water (50 ml×2), dried with anhydrous magnesium sulfate, filtered and concentrated. The resulting solid was slurried with methyl tert-butyl ether to give 9.60 g of the compound of formula IV as white solid (yield 85.6%).

Example 12

Except that the compound of formula IV in step 3) was prepared according to the following procedures, other steps were the same as those of Example 1.

To a 250 ml reaction bottle were successively added the compound of formula III prepared above (7.50 g, 33.74 mmol), isopropyl acetate (150 ml) and NaOH (2.70 g, 67.49 mmol), to which was added dropwise cyclohexanecarbonyl chloride (5.20 g, 35.47 mmol) under ice water bath. After addition, the reaction was performed for 2 h. To the reaction liquid was added 50 ml of diluted hydrochloric acid aqueous solution, which was stirred and allowed to stand. The organic layer was separated, washed with water (50 ml×2), dried with anhydrous magnesium sulfate, filtered and concentrated. The resulting solid was slurried with methyl tert-butyl ether to give 9.28 g of the compound of formula IV as white solid (yield 82.7%).

Example 13

Except that the compound of formula V in step 4) was prepared according to the following procedures, other steps were the same as those of Example 1.

To a 250 ml reaction bottle were successively added the compound of formula IV prepared above (6.10 g, 18.35 mmol), $CH_2Cl_2$ (100 ml) and TEMPO (0.03 g, 0.19 mmol) with the temperature in the bottle controlled as 5-10° C., to which was then added TCCA (4.30 g, 18.50 mmol). The temperature was raised to room temperature and the reaction was performed for 24 h with stirring. The reaction mixture was filtered and the filter cake was washed with 30 ml of $CH_2Cl_2$. The filtrate was washed with 200 ml of saturated $Na_2CO_3$ aqueous solution, washed with water (100 ml×2), dried with anhydrous magnesium sulfate, filtered and concentrated to give 5.16 g of the compound of formula V as light yellow solid (yield 85.1%).

Example 14

Except that the compound of formula V in step 4) was prepared according to the following procedures, other steps were the same as those of Example 1.

To a 1 L reaction bottle were successively added the compound of formula IV prepared above (10.50 g, 31.58 mmol), DMSO (60 ml) and $Et_3N$ (31.96 g, 315.84 mmol) with the temperature in the bottle controlled as 10-15° C., to which was then added dropwise the solution of $SO_3$-Py (30.16 g, 189.50 mmol) in DMSO (110 ml) and the reaction was performed for 10 h. To the reaction liquid was added 300 ml of water, which was extracted with $CH_2Cl_2$ (100 ml×2). The organic phase was combined, washed with water (50 ml×2), dried with anhydrous magnesium sulfate, filtered and concentrated to give 10.0 g of the compound of formula V as yellow solid (yield 95.8%).

Example 15

Except that the compound of formula V in step 4) was prepared according to the following procedures, other steps were the same as those of Example 1.

To a 500 ml reaction bottle were successively added the compound of formula IV prepared above (10.20 g, 30.68 mmol), $CH_2Cl_2$ (150 ml), 15 wt % NaBr aqueous solution (10.53 g, 15.35 mmol) and TEMPO (0.05 g, 0.32 mmol), with the temperature in the bottle controlled as 5-10° C., to which was then added dropwise the aqueous solution of $Ca(ClO)_2$ (4.61 g, 32.24 mmol) and the reaction was performed for 20 h. The aqueous layer was separated and extracted with 30 ml of $CH_2Cl_2$. The organic layer was combined, washed with sodium thiosulfate aqueous solution (100 ml×2), washed with water (100 ml×2), dried with anhydrous magnesium sulfate, filtered and concentrated to give 7.91 g of the compound of formula V as light yellow solid (yield 78.0%).

Example 16

Except that the compound of formula V in step 4) was prepared according to the following procedures, other steps were the same as those of Example 1.

To a 500 ml reaction bottle were successively added the compound of formula IV prepared above (10.20 g, 30.68 mmol), isopropyl acetate (250 ml), 15 wt % NaBr aqueous solution (10.53 g, 15.35 mmol) and TEMPO (0.05 g, 0.32 mmol), with the temperature in the bottle controlled as 5-10° C., to which was added dropwise NaClO aqueous solution (180 g, 32.24 mmol) of which the pH has been adjusted to 8-9 with saturated $NaHCO_3$ aqueous solution and the reaction was performed for 20 h. The aqueous layer was separated and extracted with 50 ml of isopropyl acetate. The organic layer was combined, washed with sodium thiosulfate aqueous solution (100 ml×2), washed with water (100 ml×2), dried with anhydrous magnesium sulfate, filtered and concentrated to give 7.65 g of the compound of formula V as light yellow solid (yield 75.5%).

Example 17

Except that the compound of formula V in step 4) was prepared according to the following procedures, other steps were the same as those of Example 1.

To a 500 ml reaction bottle were successively added the compound of formula IV prepared above (10.20 g, 30.68 mmol), methyl tert-butyl ether (300 ml), 15 wt % NaBr aqueous solution (10.53 g, 15.35 mmol) and TEMPO (0.05 g, 0.32 mmol), with the temperature in the bottle controlled as 5-10° C., to which was added dropwise NaClO aqueous solution (180 g, 32.24 mmol) of which the pH has been adjusted to 8-9 with saturated $NaHCO_3$ aqueous solution and the reaction was performed for 20 h. The aqueous layer was separated and extracted with 50 ml of methyl tert-butyl ether. The organic layer was combined, washed with sodium thiosulfate aqueous solution (100 ml×2), washed with water (100 ml×2), dried with anhydrous magnesium sulfate, filtered and concentrated to give 8.19 g of the compound of formula V as light yellow solid (yield 80.8%).

Example 18

Except that the compound of formula V in step 4) was prepared according to the following procedures, other steps were the same as those of Example 1.

To a 500 ml reactor were successively added the compound of formula IV prepared above (10.20 g, 30.68 mmol), $CH_2Cl_2$ (100 ml), $NaNO_2$ (0.21 g, 3.04 mmol), $FeCl_3$ (0.50 g, 3.08 mmol) and TEMPO (0.10 g, 0.64 mmol), and the reaction was performed for 10 h at room temperature under 0.3 MPa $O_2$. The reaction liquid was washed with sodium thiosulfate aqueous solution (50 ml×2), washed with water (50 ml×2), dried with anhydrous magnesium sulfate, filtered and concentrated to give 9.94 g of the compound of formula V as light yellow solid (yield 98.0%).

Example 19

Except that the compound of formula I Praziquantel in step 5) was prepared according to the following procedures, other steps were the same as those of Example 1.

To a 100 ml reaction bottle was added methanesulfonic acid (20 ml), to which were added dropwise the solution of the compound of formula V prepared above (5.40 g, 16.34 mmol) in $CH_2Cl_2$ (10 ml) under ice water bath. After addition, the temperature was raised to room temperature and the reaction was performed for 10 h. The reaction liquid was poured into 100 ml of ice water and extracted with $CH_2Cl_2$ (50 ml×2). The organic phase was combined, washed with 50 ml of saturated $Na_2CO_3$ aqueous solution, washed with water (50 ml×2), dried with anhydrous magnesium sulfate, filtered and concentrated to give light yellow solid, which was recrystallized with ethanol to give 4.27 g of the compound of formula I Praziquantel as white solid (HPLC purity 99.83%, yield 83.6%).

Example 20

Except that the compound of formula I Praziquantel in step 5) was prepared according to the following procedures, other steps were the same as those of Example 1.

To a 100 ml reaction bottle was added trifluoroacetic acid (15 ml), to which were added dropwise the solution of the compound of formula V prepared above (5.40 g, 16.34 mmol) in $CH_2Cl_2$ (10 ml) under ice water bath. After addition, the temperature was raised to room temperature and the reaction was performed for 10 h. The reaction liquid was poured into 100 ml of ice water and extracted with $CH_2Cl_2$ (50 ml×2). The organic phase was combined, washed with 50 ml of saturated $Na_2CO_3$ aqueous solution, washed with water (50 ml×2), dried with anhydrous magnesium sulfate, filtered and concentrated to give light yellow solid, which was recrystallized with ethanol to give 3.92 g of the compound of formula I Praziquantel as white solid (HPLC purity 99.93%, yield 76.8%).

Example 21

Except that the compound of formula I Praziquantel in step 5) was prepared according to the following procedures, other steps were the same as those of Example 1.

To a 100 ml reaction bottle was added trifluoromethanesulfonic acid (20 ml), to which were added dropwise the solution of the compound of formula V prepared above (5.40 g, 16.34 mmol) in $CH_2Cl_2$. (10 ml) under ice water bath. After addition, the temperature was raised to room temperature and the reaction was performed for 10 h. The reaction liquid was poured into 100 ml of ice water and extracted with $CH_2Cl_2$ (50 ml×2). The organic phase was combined, washed with 50 ml of saturated $Na_2CO_3$ aqueous solution, washed with water (50 ml×2), dried with anhydrous magnesium sulfate, filtered and concentrated to give light yellow solid, which was recrystallized with ethanol to give 3.60 g of the compound of formula I Praziquantel as white solid (HPLC purity 99.86%, yield 70.5%).

Example 22

Except that the compound of formula I Praziquantel in step 5) was prepared according to the following procedures, other steps were the same as those of Example 1.

To a 100 ml reaction bottle was added benzenesulfonic acid (20 ml), to which were added dropwise the solution of the compound of formula V prepared above (5.40 g, 16.34 mmol) in $CH_2Cl_2$ (10 ml) under ice water bath. After addition, the temperature was raised to room temperature and the reaction was performed for 10 h. The reaction liquid was poured into 100 ml of ice water and extracted with $CH_2Cl_2$ (50 ml×2). The organic phase was combined, washed with 50 ml of saturated $Na_2CO_3$ aqueous solution, washed with water (50 ml×2), dried with anhydrous magnesium sulfate, filtered and concentrated to give light yellow solid, which was recrystallized with ethanol to give 3.71 g of the compound of formula I Praziquantel as white solid (HPLC purity 99.85%, yield 72.7%).

Example 23

Except that the compound of formula I Praziquantel in step 5) was prepared according to the following procedures, other steps were the same as those of Example 1.

To a 100 ml reaction bottle was added concentrated sulfuric acid (15 ml), to which were added dropwise the solution of the compound of formula V prepared above (5.60 g, 16.95 mmol) in toluene (15 ml) under ice water bath and the reaction was performed for 8 h. The reaction liquid was poured into 150 ml of ice water and extracted with toluene (50 ml×2). The organic phase was combined, washed with 50 ml of saturated. $Na_2CO_3$ aqueous solution, washed with water (50 ml×2), dried with anhydrous magnesium sulfate, filtered and concentrated to give light yellow solid, which was recrystallized with ethanol to give 4.54 g of the compound of formula I Praziquantel as white solid (HPLC purity 99.87%, yield 85.7%).

Example 24

Except that the compound of formula I Praziquantel in step 5) was prepared according to the following procedures, other steps were the same as those of Example 1.

To a 100 ml reaction bottle was added concentrated sulfuric acid (15 ml), to which were added dropwise the solution of the compound of formula V prepared above (5.60 g, 16.95 mmol) in methyl tert-butyl ether (15 ml) under ice water bath and the reaction was performed for 8 h. The reaction liquid was poured into 150 ml of ice water and extracted with methyl tert-butyl ether (50 ml×2). The organic phase was combined, washed with 50 ml of saturated $Na_2CO_3$ aqueous solution, washed with water (50 ml×2), dried with anhydrous magnesium sulfate, filtered and concentrated to give light yellow solid, which was recrystallized with ethanol to give 4.30 g of the compound of formula I Praziquantel as white solid (HPLC purity 99.85%, yield 81.3%).

Example 25

Except that the compound of formula I Praziquantel in step 5) was prepared according to the following procedures, other steps Were the same as those of Example 1.

To a 100 ml reaction bottle was added concentrated sulfuric acid (15 ml), to which were added dropwise the solution of the compound of formula V prepared above (5.60 g, 16.95 mmol) in isopropyl acetate (15 ml) under ice water bath and the reaction was performed for 8 h. The reaction liquid was poured into 150 ml of ice water and extracted with isopropyl acetate (50 ml×2). The organic phase was combined, washed with 50 ml of saturated $Na_2CO_3$ aqueous solution, washed with water (50 ml×2), dried with anhydrous magnesium sulfate, filtered and concentrated to give light yellow solid, which was recrystallized with ethanol to give 4.27 g of the compound of formula I Praziquantel as white solid (HPLC purity 99.91%, yield 80.6%).

Although typical embodiments have been illustrated herein, the invention should not be limited to the detailed description above. Possible amendments and substitutions can be made to the invention without departing from the spirit thereof. Accordingly, a person skilled in the art can think of modifications and equivalence with conventional experiments and such modifications and equivalence are within the spirit and scope of the invention defined by the appended claims.

The invention claimed is:

1. An intermediate compound for preparing Praziquantel, having the structure of formula IV:

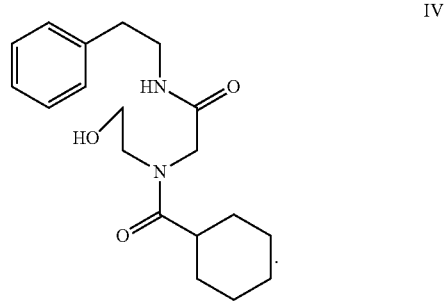 [SMILES: O=C(CN(CCO)C(=O)C1CCCCC1)NCCc1ccccc1]

2. A process for preparing the intermediate compound of formula IV according to claim 1, comprising steps of:

(i) subjecting β-phenethylamine and chloroacetyl chloride to a condensation reaction in the presence of an alkaline substance to give a compound of formula II:

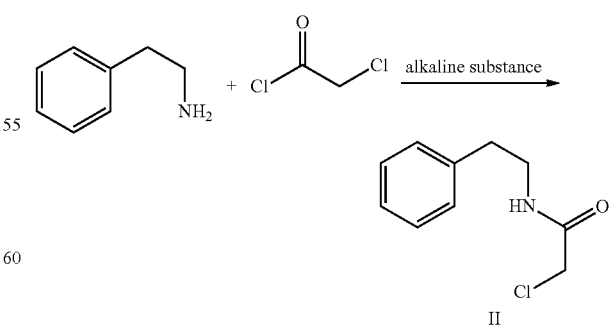

(ii) subjecting the compound of formula II and ethanolamine to a substitution reaction to give a compound of formula III: and

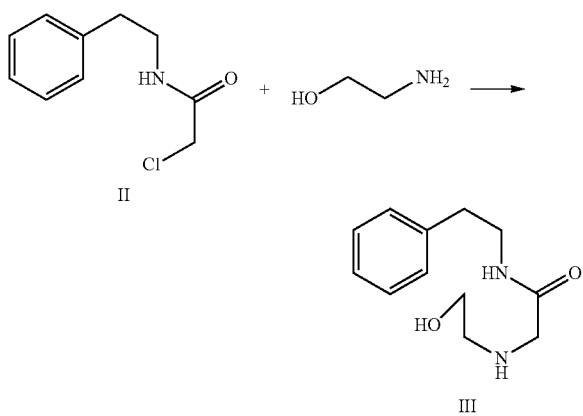

II

III (iii) subjecting the compound of formula III and cyclohexanecarbonyl chloride to an acylation reaction in the presence of an alkaline substance to give the compound of formula IV:

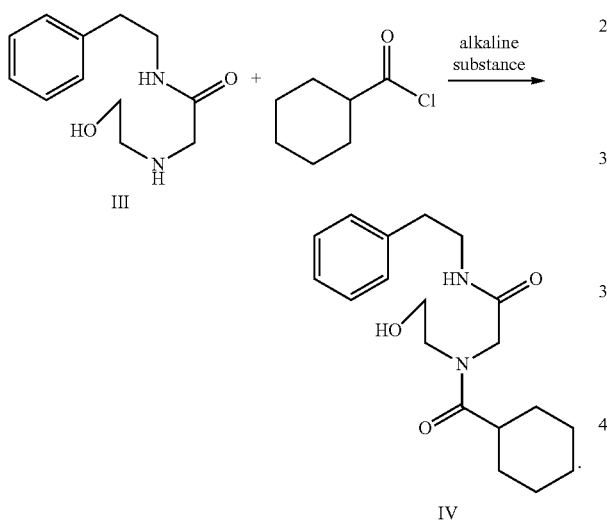

IV

3. The preparing process according to claim 2, wherein the alkaline substance in step (i) and step (iii) is at least one each independently selected from the group consisting of triethylamine, imidazole, pyridine, 2-methylpyridine, 2,6-dimethylpyridine, 4-dimethylaminopyridine, diisopropylamine, dimethylisopropylamine, diisopropylethylamine, NaOH, $Na_2CO_3$, $NaHCO_3$, KOH and $K_2CO_3$.

4. The preparing process according to claim 2, wherein the molar ratio of the compound of formula II to ethanolamine in step (ii) is 1:2-1:15.

5. The preparing process according to claim 2, wherein step (i), step (ii), or step (iii) is performed without solvent or performed with at least one aprotic organic solvent as reaction solvent.

6. The preparing process according to claim 5, wherein the aprotic organic solvent is at least one selected from the group consisting of ethers solvent, aromatic hydrocarbons solvent, hydrocarbons or halogenated hydrocarbons solvent and esters solvent.

7. The preparing process according to claim 6, wherein the ethers solvent is selected from the group consisting of tetrahydrofuran, diethyl ether, 1,2-dimethoxylethane, methyl tert-butyl ether and 2-methyltetrahydrofuran;
the aromatic hydrocarbons solvent is selected from the group consisting of benzene, toluene, ethylbenzene and xylene;
the hydrocarbons or halogenated hydrocarbons solvent is selected from the group consisting of n-hexane, cyclohexane, n-heptane, dichloromethane, trichloromethane and dichloroethane;
the esters solvent is selected from the group consisting of methyl formate, ethyl formate, methyl acetate, ethyl acetate and isopropyl acetate.

8. The preparing process according to claim 2, wherein the reaction temperature of step (i), step (ii), or step (iii) is −10° C. to 100° C.

9. The preparing process according to claim 3, wherein the alkaline substance in step (i) and step (iii) is at least one each independently selected from the group consisting of triethylamine, NaOH, $Na_2CO_3$, $NaHCO_3$, KOH and $K_2CO_3$.

10. The preparing process according to claim 4, wherein the molar ratio of the compound of formula II to ethanolamine in step (ii) is 1:3-1:8.

11. The preparing process according to claim 7, wherein the ethers solvent is methyl tert-butyl ether;
the aromatic hydrocarbons solvent is toluene;
the hydrocarbons or halogenated hydrocarbons solvent is dichloromethane; and
the esters solvent is ethyl acetate or isopropyl acetate.

12. The preparing process according to claim 8, wherein the reaction temperature of step (i), step (ii), or step (iii) is 0° C. to 40° C.

13. The preparing process according to claim 8, wherein the reaction temperature of step (i), step (ii), or step (iii) is 5° C. to 15° C.

14. The preparing process according to claim 8, wherein the reaction temperature of step (i), step (ii), or step (iii) is 10° C. to 15° C.

* * * * *